(12) United States Patent
Lin

(10) Patent No.: US 9,186,085 B2
(45) Date of Patent: Nov. 17, 2015

(54) WEARABLE ASSEMBLY FOR MEASURING BIO-IMPEDANCE

(71) Applicant: CHUNG HUA UNIVERSITY, Hsinchu (TW)

(72) Inventor: Jium Ming Lin, Hsinchu (TW)

(73) Assignee: CHUNG HUA UNIVERSITY, Hsinchu (TW)

( * ) Notice: Subject to any disclaimer, the term of this patent is extended or adjusted under 35 U.S.C. 154(b) by 0 days.

(21) Appl. No.: 14/340,847

(22) Filed: Jul. 25, 2014

(65) Prior Publication Data

US 2014/0336492 A1    Nov. 13, 2014

Related U.S. Application Data

(62) Division of application No. 13/291,713, filed on Nov. 8, 2011, now Pat. No. 8,825,150.

(30) Foreign Application Priority Data

Nov. 9, 2010   (TW) ................................ 99138437 A

(51) Int. Cl.
*A61B 5/05* (2006.01)
*A61B 5/053* (2006.01)
*A61B 5/00* (2006.01)
*A61N 1/36* (2006.01)

(52) U.S. Cl.
CPC ............. *A61B 5/0532* (2013.01); *A61B 5/0022* (2013.01); *A61B 5/6806* (2013.01); *A61B 5/6807* (2013.01); *A61B 5/7257* (2013.01); *A61N 1/36017* (2013.01); *A61B 2560/0425* (2013.01); *A61B 2560/0431* (2013.01)

(58) Field of Classification Search
CPC .................................................... A61B 5/0532
USPC .............. 600/547, 548, 365; 340/572.4, 10.4, 340/10.1, 572.7, 10.42; 601/6; 40/118; 604/173; 257/758–760, 499, 750, 257/E23.144; 375/130
See application file for complete search history.

(56) References Cited

U.S. PATENT DOCUMENTS

| | | | | |
|---|---|---|---|---|
| 3,619,923 A | * | 11/1971 | Bruner | 40/118 |
| 6,903,459 B2 | * | 6/2005 | Nakatani | 257/758 |
| 2004/0092839 A1 | * | 5/2004 | Shin et al. | 600/547 |
| 2005/0209565 A1 | * | 9/2005 | Yuzhakov et al. | 604/173 |
| 2007/0156040 A1 | * | 7/2007 | Mouradian et al. | 600/365 |
| 2008/0167585 A1 | * | 7/2008 | Khen et al. | 601/6 |
| 2008/0180253 A1 | * | 7/2008 | Ovard et al. | 340/572.4 |
| 2011/0082383 A1 | * | 4/2011 | Cory et al. | 600/547 |

* cited by examiner

*Primary Examiner* — Brian Szmal
(74) *Attorney, Agent, or Firm* — WPAT, P.C.; Anthony King

(57) ABSTRACT

A bio-impedance measurement apparatus includes a flexible band member, two probe sets attached to the flexible band member, a measurement device, and a wireless device. One probe set includes a probe having a tip portion configured to pierce the skin for an acupuncture point. Another probe set, used as an electrical ground, includes a probe configured to contact the reference skin at a region. The measurement device is disposed on the flexible band member and electrically coupled to the two probe sets for provision of an impulse current signal to the acupuncture point. The measurement device can amplify and measure the voltage response across the acupuncture points and the ground. The amplified signal is converted to a digital signal. The wireless device is configured to transmit the acupuncture code and impedance information to a remote monitor station. The bio-impedance measurement apparatus is disposed on a wearable sock or glove.

7 Claims, 19 Drawing Sheets

WEARABLE ASSEMBLY FOR MEASURING BIO-IMPEDANCE

CROSS-REFERENCE TO RELATED APPLICATION

The present application is a divisional application of U.S. patent application Ser. No. 13/291,713, now allowed, which claims benefit of priority to Taiwan Patent Application Serial Number 099138437, filed on Nov. 9, 2010, the disclosure of which is hereby incorporated by reference herein in its entirety.

BACKGROUND OF THE INVENTION

1. Field of the Invention

The present invention relates to a bio-impedance measurement apparatus, and relates more particularly to a bio-impedance measurement apparatus having wireless communication capability.

2. Description of the Related Art

During the 1950s, Dr. Reinhard Voll studied acupuncture points and discovered there are nearly 2000 acupuncture points on the skin of a human body, and those acupuncture points are distributed along the paths called meridians. In accordance with traditional Chinese medicine theory, the meridians are channels for transmission of energy, and the transmitted energy is known as "chi." Western research discovered that acupuncture points can be identified by low direct current resistance of the skin. In other words, acupuncture points are specific superficial anatomic locations. At these locations, the skin resistance is lower than that of the surrounding skin. Dr. Voll further discovered that organ health can be determined by the measurement of the impedance of acupuncture points corresponding to specific organs. In addition, electric therapy studies showed that when therapy signals are repetitively directed into acupuncture points, the impedance of the acupuncture points can be restored, and the corresponding organs can be treated.

U.S. Pat. No. 4,981,146, U.S. Pat. No. 5,397,338, U.S. Pat. No. 5,626,617, U.S. Pat. No. 6,735,480 and U.S. Patent Application Publication No. 2005/0,197,555 disclose treatment methods or methods of monitoring the health of human bodies using acupuncture points. Conventionally, a bio-impedance measuring device and a metal probe are applied to measure the impedance of acupuncture points. Such measurement is non-invasive and the metal probe does not pierce the subject's body, and one acupuncture point can be measured in each measurement. However, the accuracy of traditional bio-impedance measuring devices is adversely affected by poor electrical contact between the probe and the skin. Usually, when one acupuncture point is measured, several measurements at different nearby locations are required so as to obtain stable and reliable skin resistance information.

As shown in FIGS. 1 to 3, Dr. Voll discovered many electrically conductive points (acupuncture points) on the hands and feet of the human body. Because traditional bio-impedance measuring devices can manually measure only one acupuncture point at a time, thus measuring the acupuncture points of hands and feet of a human subject to obtain stable and reliable skin resistance information is very time-consuming.

Furthermore, acupuncture points lie under the thick cuticle of the skin so that impedance is often measured higher than its true value, causing erroneous measuring results.

Due to the disadvantages of traditional bio-impedance measuring devices, a new, more efficient and reliable bio-impedance measuring device is needed.

SUMMARY OF THE INVENTION

One objective of the present invention is to provide a bio-impedance measurement apparatus including a probe configured to pierce the skin for accurate measurement of acupuncture point impedance.

Another objective of the present invention is to provide a bio-impedance measurement apparatus including a wireless device disposed for transmitting acupuncture point codes and impedance information to a remote control station for analysis.

Yet another objective of the present invention is to provide an assembly of a plurality of bio-impedance measurement apparatuses and a plurality of wireless devices wearable on the body and configured to simultaneously measure the impedance of plural acupuncture points.

In accordance with the above and other objectives, the present invention proposes a bio-impedance measurement apparatus comprising a flexible band member, two probe sets, a measurement device, and a wireless device. The flexible band member is configured to be fastened around a body portion, comprising an inner surface disposed adjacent to a skin region of the body portion when the flexible band member is fastened to the body portion. The two probe sets are attached to the flexible band member. Each probe set comprises a probe, wherein the probe of one probe set includes a tip portion configured to protrude from the inner surface to pierce the skin so as to be located adjacent to an acupuncture point, and the probe of another probe set is configured to contact the reference skin as an electrical ground. The measurement device is disposed on the flexible band member, electrically coupled to the two probe sets, and configured to provide a pulse current signal to the acupuncture point and to measure impedance of the acupuncture point. The wireless device is coupled to the measurement device, configured to transmit an acupuncture code corresponding to the acupuncture point and the impedance information of the acupuncture point to the remote monitor station In one embodiment, the measurement device provides an impulse current signal to the acupuncture point, causing a voltage generated between the acupuncture point and the electrical ground. The measurement device can amplify the voltage signal and convert the amplified signal into a digital signal using an analog/digital converter. The measurement device can obtain the impedance of the acupuncture point by performing a Fourier transformation of the digital signal.

In one embodiment, the measured voltage signal can be transmitted to a remote control station, which performs a Fourier transformation to obtain the impedance of the acupuncture point.

One embodiment of the present invention provides a wearable assembly for measuring bio-impedance comprising a glove and the above-mentioned bio-impedance measurement apparatus. The glove comprises a plurality of finger and wrist portions, and the bio-impedance measurement apparatus is disposed on a finger portion and a wrist portion.

Another embodiment of the present invention provides a wearable assembly for measuring bio-impedance comprising a sock and the above-mentioned bio-impedance measurement apparatus disposed on the sock.

To better understand the above-described objectives, characteristics and advantages of the present invention, embodiments, with reference to the drawings, are provided for detailed explanations.

BRIEF DESCRIPTION OF THE DRAWINGS

The invention will be described according to the appended drawings in which.

DETAILED DESCRIPTION OF THE INVENTION

Figure 4:
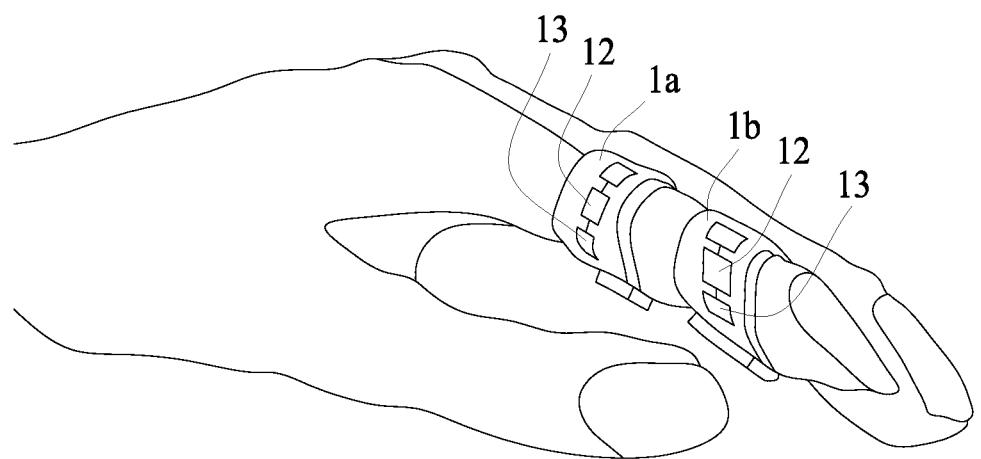
FIG. 4 is a view showing a bio-impedance measurement apparatus according to one embodiment of the present invention.
Figure 5:
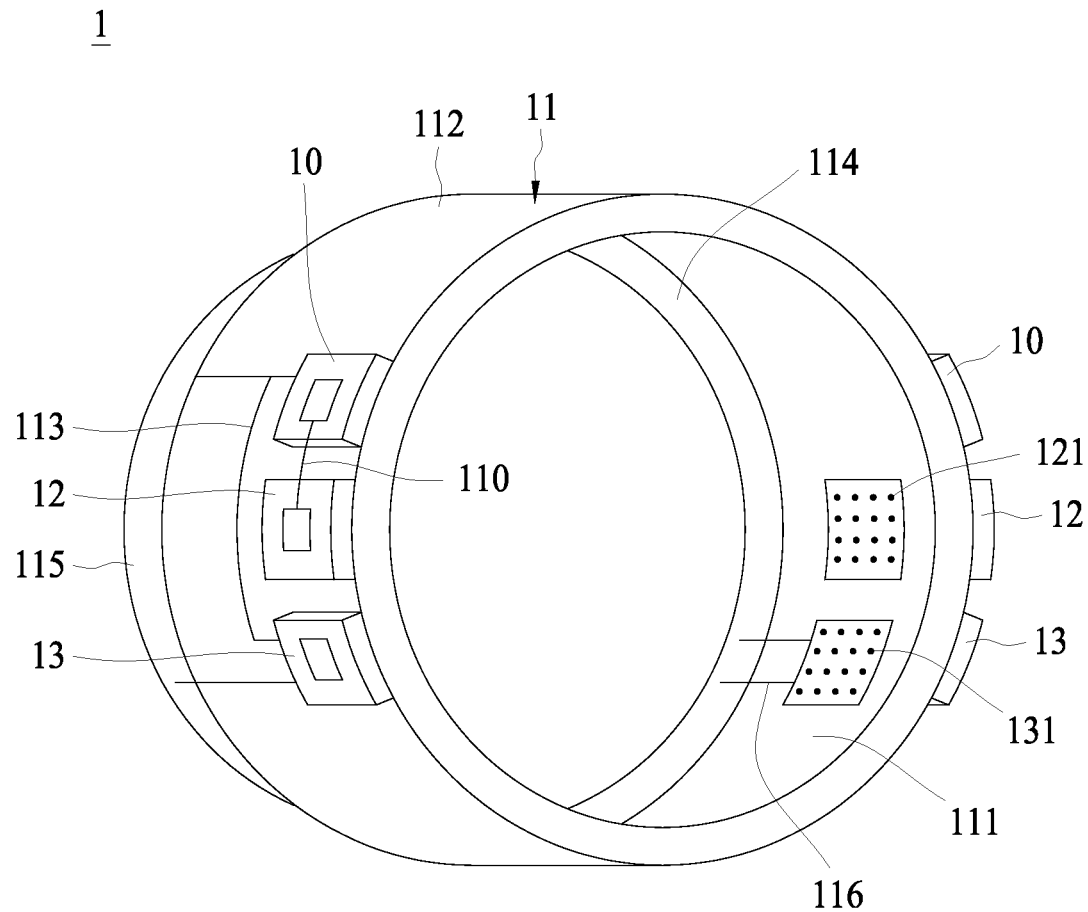
FIG. 5 is a perspective view showing a bio-impedance measurement apparatus according to one embodiment of the present invention.
Figure 6:
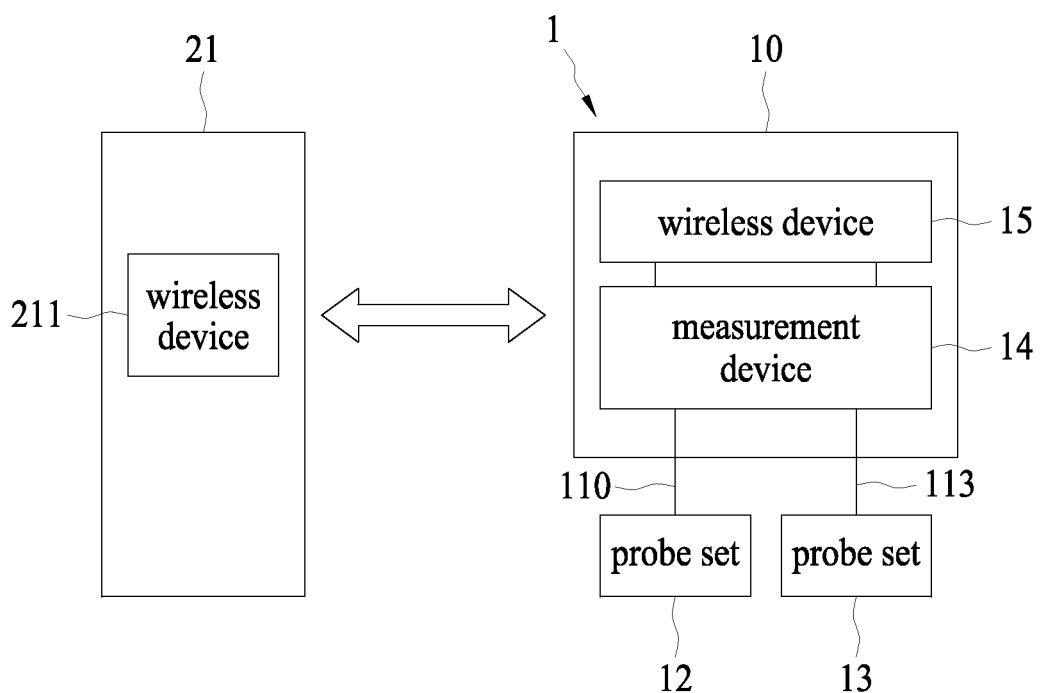
FIG. 6 is a perspective view showing a bio-impedance measurement apparatus according to one embodiment of the present invention.

FIG. 4 is a view showing a bio-impedance measurement apparatus according to one embodiment of the present invention. FIG. 5 is a perspective view showing a bio-impedance measurement apparatus according to one embodiment of the present invention, in which the chip device 10 and probe sets 12 and 13 are on a flexible band member 11. FIG. 6 is a perspective view showing a bio-impedance measurement apparatus 1 according to one embodiment of the present invention. FIG. 6 is a view showing a bio-impedance measurement system 2 according to one embodiment of the present invention. The bio-impedance measurement apparatus 1 comprises a flexible band member 11, two probe sets 12 and 13, and a chip device 10.

The flexible band member 11 as in FIG. 5 is configured to be fastened around a body portion such as a head, a limb, a trunk, a shoulder, a neck, a finger or a toe. The flexible band member 11 includes an inner surface 111 that is adjacent to a skin region of the body portion when the flexible band member 11 is fastened to the body portion. The flexible band member 11 can be a ring member that can be directly worn on limbs, fingers, a trunk, or toes. The flexible band member 11 can include free distal ends (e.g. a rope), configured to be wrapped around a body portion.

The pair of probe sets 12 and 13 is attached to the flexible band member 11. In the present embodiment, the probe sets 12 and 13 are configured to measure the impedance of acupuncture points. The probe set 12 and the probe set 13 can be separated from each other, and are configured to contact or pierce the skin and form a loop circuit for measuring impedance of acupuncture points.

Figure 10:
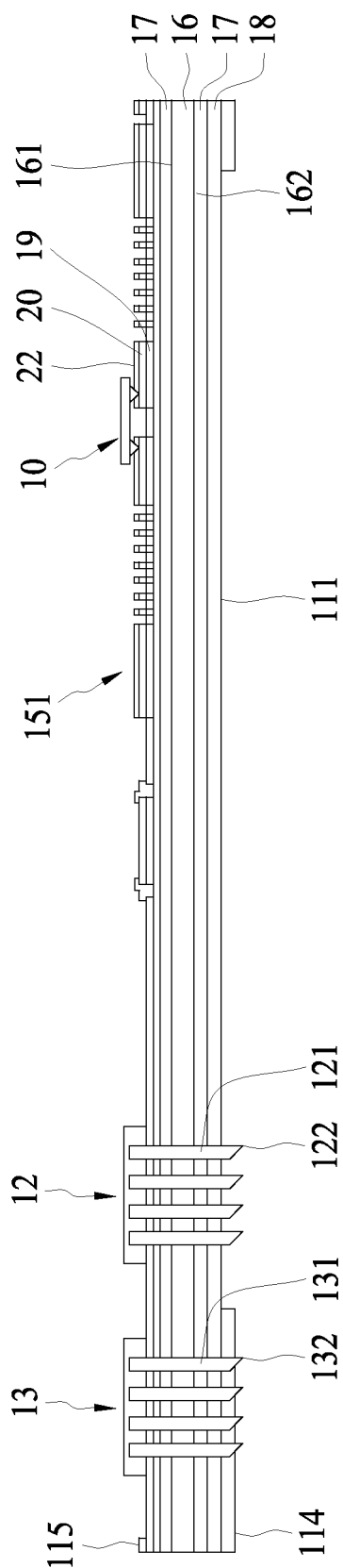
FIG. 10 is a cross-sectional view along the line 5-5 of FIG. 9.

Referring to FIG. 10, the probe set 12 may comprise at least one probe 121 comprising a tip portion 122 configured to protrude from the inner surface 111 and be able to pierce the skin so as to be located adjacent to an acupuncture point to be measured. In particular, the tip portion 122 can be trimmed to include a surface inclined at an angle of from 5 to 55 degrees, forming a sharp point so that the tip portion 122 can easily pierce the skin. In one embodiment, the tip portion 122 can be trimmed at an angle of 45 degrees. If the trimming angle is too small, the contact area between the probe and the skin will be reduced, increasing measured impedance. If the trimming angle is too large, the piercing depth will be adversely affected, increasing measured impedance as well. Furthermore, the tip portion 122 is can be configured to pierce into a specific skin layer such as the dermis so that accurate measurements can be obtained. Similarly, the probe set 13 can comprise at least one probe 131, which may comprise a tip portion 132 configured to protrude from the inner surface 111 of the flexible band member 11. The tip portion 132 can contact the skin or pierce the skin. Likewise, the tip portion 132 can be trimmed to include a surface inclined at an angle of from 5 to 55 degrees, forming a sharp point so that the tip portion 132 can easily pierce the skin. If the trimming angle is too small, the contact area between the probe and the skin will be reduced, increasing measured impedance. If the trimming angle is too large, the piercing depth will be adversely affected, increasing measured impedance as well. The probes 121 and 131 can be made of material compatible with the skin. The probes 121 and 131 can include a coating. The probes 121 and 131 can comprise material coated with a coating, wherein the material is stainless steel, tungsten, or nickel chromium, and the coating is gold, titanium nitride, or titanium.

Figure 1:
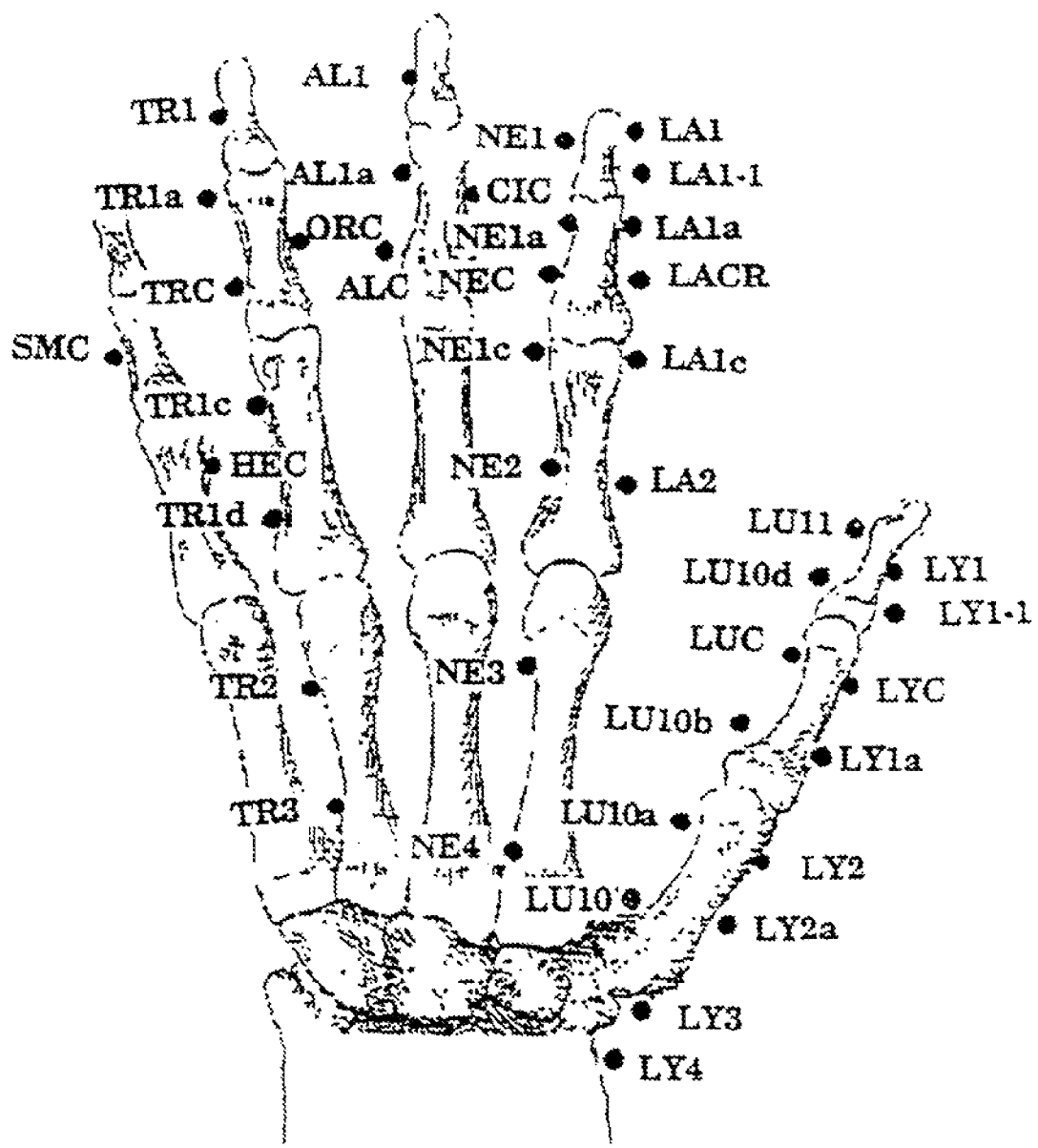
FIGS. 1 to 3 show electrically conductive points (acupuncture points) on a hand and a foot, discovered by Dr. Reinhard Voll.

Referring to FIGS. 1, 4, and 5, the bio-impedance measurement apparatus 1 may comprise two pairs of probe sets 12 and 13 disposed in accordance with acupuncture points. In one embodiment, the two probe sets 12 of the embodiment of FIG. 5 can be disposed in accordance with the acupuncture point NE2 and the acupuncture point LA2, and another pair of probe sets 13 can be disposed at positions where no acupuncture point is located such that when the bio-impedance measurement apparatus 1 is worn on an index finger, the impedance of the acupuncture points NE2 and LA2 can be measured simultaneously. In another embodiment, the apparatus of FIG. 4 comprises two pairs of bio-impedance measurement apparatuses 1a and 1b, in which two pairs of probe sets 12 are disposed in accordance with the acupuncture points LA1a and LA2, and another two pairs of probe sets 13 are disposed at positions where no acupuncture point is located such that when the bio-impedance measurement apparatuses 1a and 1b are worn on an index finger, the impedance of the acupuncture points LA2 and LA1a can be measured simultaneously.

Further, each probe set 12 or 13 can comprise a plurality of probes 121 and 131. The plurality of probes 121 or 131 can be arranged in an array.

Referring to FIGS. 5 and 6, the chip device 10 can be disposed on the outer surface 112 of the flexible band member 11, connected with the corresponding probe sets 12 and 13 by conductive wires 110 and 113 disposed on the outer surface 112.

Referring to FIG. 6, the chip device 10 may comprise a measurement device 14 and a wireless device 15. The measurement device 14 is electrically coupled to the two probe sets 12 and 13 by conductive wires 110 and 113, which are configured to provide impulse current signals required to measure the impedance of acupuncture points. Meanwhile, the measurement device 14 can detect the voltage response signals between acupuncture points and electrical ground, and amplify the voltage response signals. The amplified voltage response signals are sampled by an analog/digital converter and converted into digital signals which are then processed by Fourier transformation in the measurement device 14. Finally, the impedance between acupuncture points and the electrical ground can be obtained. The wireless device 15 in FIG. 6 may be coupled to the measurement device 14, thereby transmitting the code of a measured acupuncture point and its impedance to a remote control monitor station 21. Although the present embodiment demonstrates that the measurement device 14 and the wireless device 15 are integrated into the chip device 10, the present invention is not limited to such an arrangement. In another embodiment, the sampled voltage signals are directly transmitted to the remote controlling monitor station 21 without any processing, and the received signals are then processed by Fourier transformation to obtain the code and the impedance of the measured acupuncture point.

Referring to FIG. 5, the bio-impedance measurement apparatus 1 may further comprise two metal layers 114 and 115 used as ground reference points. The two metal layers 114 and 115 can be respectively disposed on the inner surface 111 and the outer surface 112 of the flexible band member 11, and coupled to the two probe sets 13 using the conductive wires 113 and 116, wherein the metal layer 114 on the inner surface 111 can be configured to contact the skin but does not contact any acupuncture point. In one embodiment, the metal layers 114 and 115 can be adjacent to an edge of the flexible band member 11, formed along the edge. In one embodiment, the metal layers 114 and 115 may comprise gold, which provides better electrical connection to the ground and thereby improves the performance of impedance measurement.

Specifically, as shown in FIG. 6, the present invention provides another bio-impedance measurement system 2, which comprises a bio-impedance measurement apparatus 1 and a remote control monitor station 21 comprising a wireless device 211. The wireless device 211 of the remote control monitor station 21 and the wireless device 15 of the bio-impedance measurement apparatus 1 can communicate with each other by a wireless communication protocol. The communication protocol may define the names and codes of acupuncture points and the format of impedance information so that communicated information can be demodulated and identified. The remote control monitor station 21 can receive, store and analyze the codes and impedance information of acupuncture points transmitted from the bio-impedance measurement apparatus 1. The remote control monitor station 21 can remotely control the bio-impedance measurement apparatus 1 to trigger the bio-impedance measurement apparatus 1 to provide impulse currents to an acupuncture point for measuring the impedance of the acupuncture point, or to provide treatment to the acupuncture point.

In one embodiment, the wireless device 211 of the remote control monitor station 21 and the wireless device 15 of the bio-impedance measurement apparatus 1 can be RFID (Radio Frequency Identification) devices.

In another embodiment, the wireless device 211 of the remote control monitor station 21 and the wireless device 15 of the bio-impedance measurement apparatus 1 can be Zigbee devices or Bluetooth devices.

Figure 7:
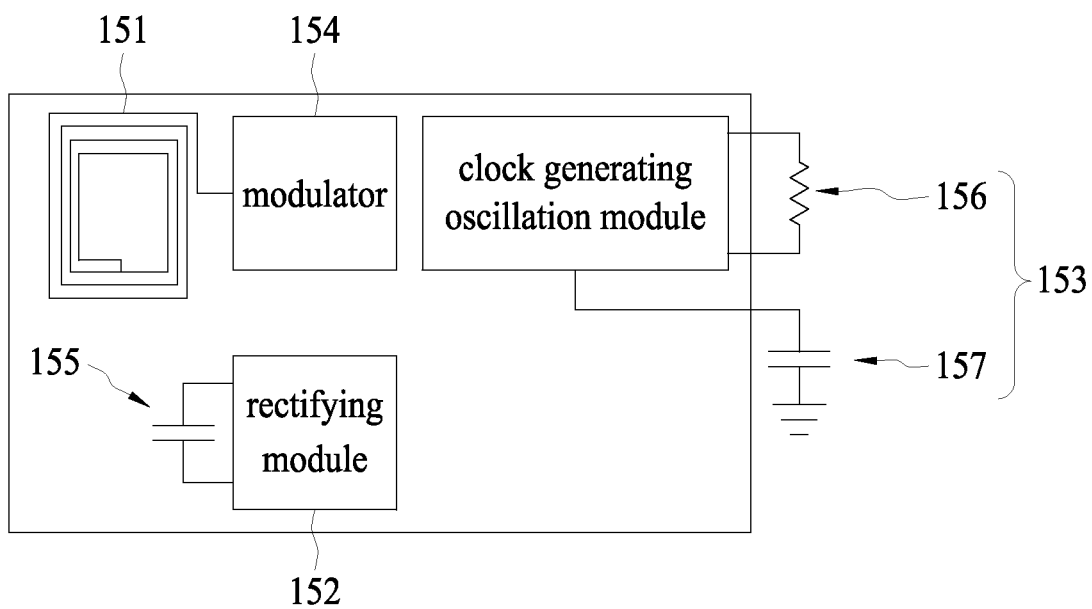
FIG. 7 is a view showing a wireless device according to one embodiment of present invention.

FIG. 7 is a view showing a wireless device according to one embodiment of present invention. The wireless device 15 may be an RFID device. The wireless device 15 can be coupled to an antenna 151 and comprise a rectifying module 152, an oscillating module 153 for generating clock signals, and a modulator 154. The rectifying module 152 may be coupled to the antenna 151 and configured to convert microwave energy signals received by the antenna 151 into DC electricity. The rectifying module 152 can be configured to supply electricity to the RFID wireless device 15 when the RFID wireless device 15 is operated in a passive mode. The oscillating module 153 may be coupled to the antenna 151 and configured to provide clock signals to the bio-impedance measurement apparatus 1. The modulator 154 may be coupled to the antenna 151 and configured to modulate transmitting signals and/or demodulate received signals.

In particular, the rectifying module 152 can be coupled to a capacitor 155 for stabilizing electricity supply. In addition, the oscillating module 153 may comprise a resistor 156 and a capacitor 157. Alternatively, the oscillating module 153 may be a multi-vibrator. The antenna 151, resistor 156, and the capacitor 157 can be manufactured on the flexible band member 11, and the manufacturing method can refer to Taiwan Patent to application Ser. No. 09/812,3308, the original counterpart patent application of U.S. patent application Ser. No. 12/767,592.

Figure 8:
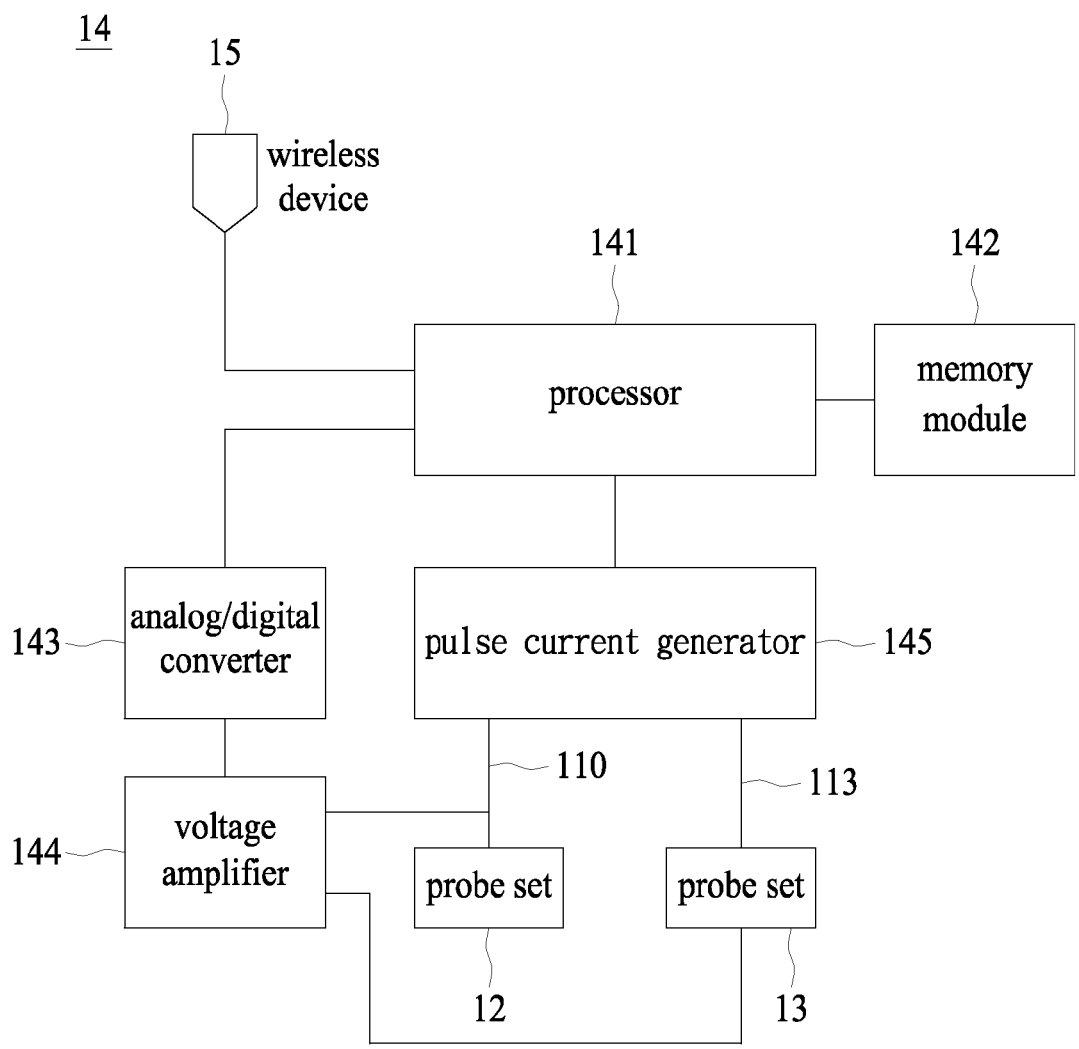
FIG. 8 is a view showing a measurement device according to one embodiment of the present invention.

FIG. 8 is a view showing a measurement device 14 according to one embodiment of the present invention. The measurement device 14 may comprise a processor 141, a memory module 142, an analog/digital converter 143, a voltage amplifier 144, and a pulse current generator 145. The probe sets 12 and 13 are individually coupled to the pulse current generator 145 by conductive wires 110 and 113. The voltage response signals produced after acupuncture points receive impulse current signals are initially transmitted to the voltage amplifier 144, and then transmitted to the analog/digital converter 143, which samples analog signals from the voltage amplifier 144 and converts them to digital signals, which are then transmitted to the processor 141. The processor 141 is configured to perform Fourier transformation and thereby processes the voltage response signals produced after acupuncture points receive impulse current signals provided by the bio-impedance measurement apparatus 1 to calculate the impedance of the acupuncture points. Further, the processor 141 may initiate the programs associated with wireless communication and keep each part of the bio-impedance measurement apparatus 1 in normal operation. The memory module 142 is coupled to the processor 141 for temporarily or permanently storing the data required for the operation of the bio-impedance measurement apparatus 1 or programs for the device. For example, the memory module 142 stores the data such as measured impedance information of acupuncture points, impulse current signal information for acupuncture points, operating programs for the bio-impedance measurement apparatus 1, and a Fourier transformation program. In another embodiment, sampled voltages are directly transmitted to the remote control monitor station 21, and then converted by Fourier transformation. Consequently, the impedance information between acupuncture points and ground reference can be obtained. The probe sets 12 and 13, coupled to the pulse current generator 145, are configured to measure the impedance between acupuncture points and electrical ground. The pulse current generator 145 can communicate with the voltage amplifier 144 so that the voltage amplifier 144 can amplify the voltage signals produced on the probe sets 12 and 13 coupled to the pulse current generator 145. The voltage amplifier 144 can be coupled with the analog/digital converter 143, which can convert the analog signals from the voltage amplifier 144 into digital signals.

Figure 15:
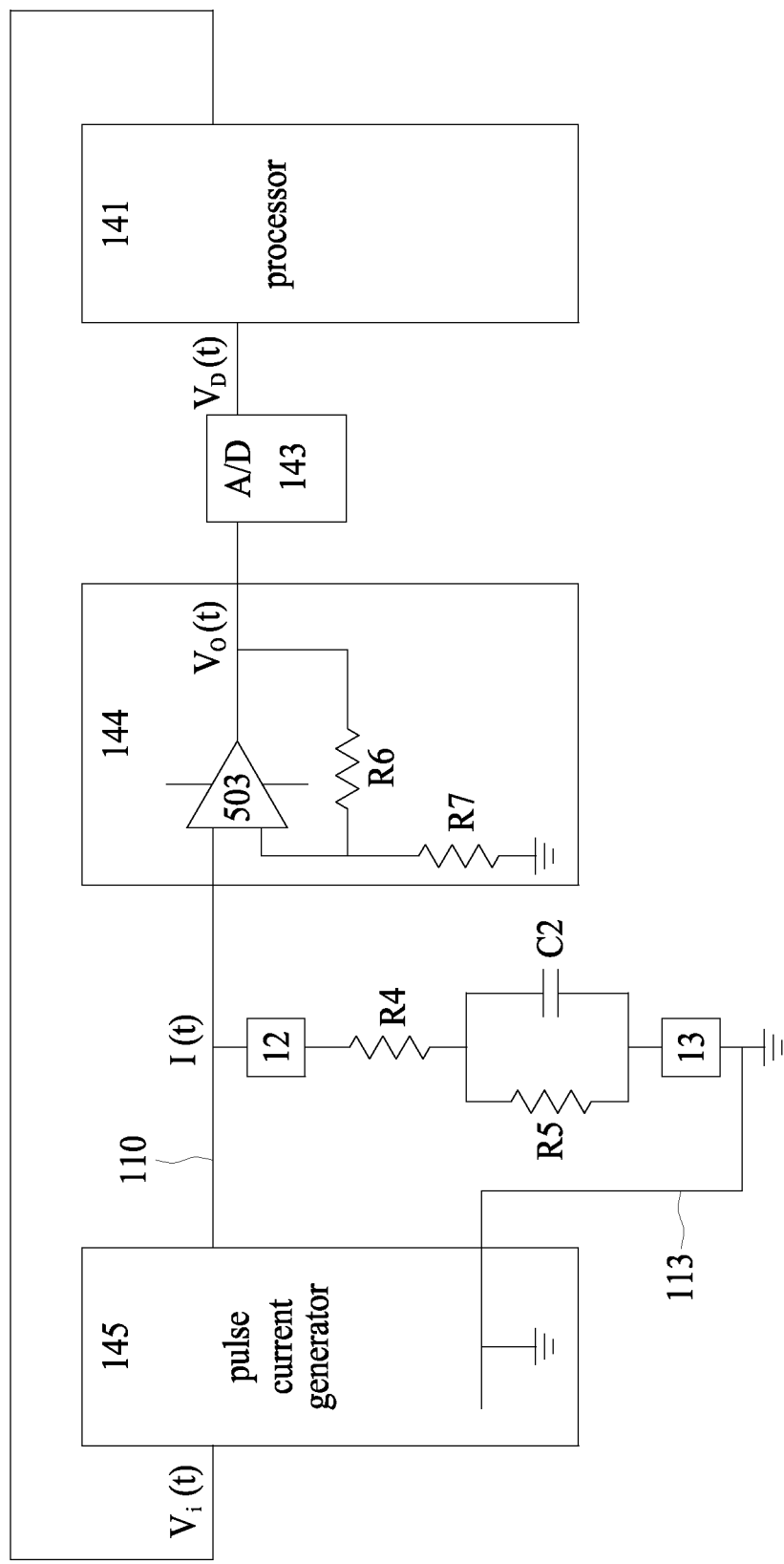
FIG. 15 is a schematic view showing a measurement device according to one embodiment of the present invention.

Referring to FIG. 15, in one embodiment, the processor 141 can send a voltage signal $V_i(t)$ to the pulse current generator 145 for generating impulse current I(t) in a range of from 1 microampere to 100 microamperes, which is supplied to acupuncture points via the conductive wire 110 and the probe set 12. In addition, the ground terminal of the pulse current generator 145 is connected to the probe set 13 via the conductive wires 113. The impulse current I(t) flows through an acupuncture point having impedance that can be represented by an equivalent circuit including a capacitor C2 and resistors R4 and R5, causing a voltage drop. This voltage can be amplified to an output voltage $V_o(t)$ by a voltage amplifier such as an operational amplifier 503 including resistors R6 and R7. The voltage $V_o(t)$ is then transmitted to the analog/digital converter 143, converting it into a sampled digital signal $V_D(t)$, which is then sent to the processor 141.

Figure 9:
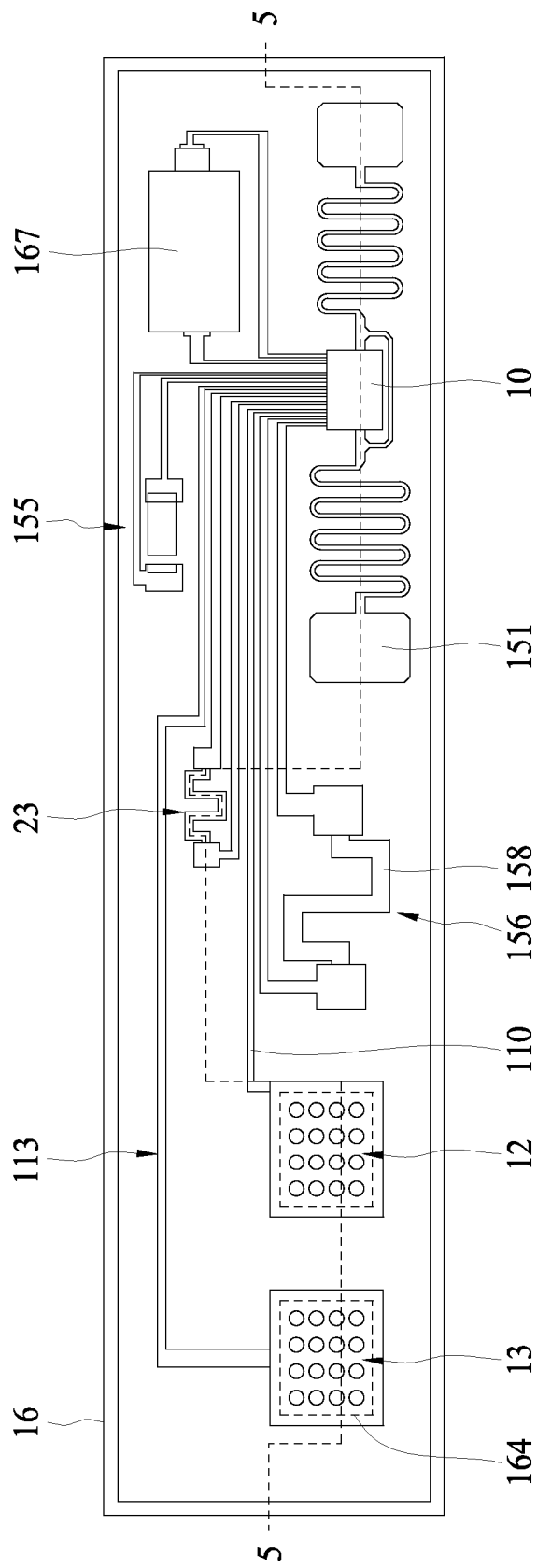
FIG. 9 is a view showing a layout of a bio-impedance measurement apparatus according to one embodiment of the present invention.

FIG. 9 is a view showing a layout of a bio-impedance measurement apparatus 1 according to one embodiment of the present invention. FIG. 10 is a cross-sectional view along the line 5-5 of FIG. 9. The bio-impedance measurement apparatus 1 can be manufactured on a flexible substrate 16 including a first surface 161 and a second surface 162, on each of which silicon dioxide and silicon nitride layers 17 can be formed for heat and water resistance. A photoresist layer 18 is formed on the silicon dioxide and silicon nitride layer 17 on the second surface 162 for preventing the silicon dioxide and silicon nitride layers 17 from moisture. Chromium and nickel layers 19 and 20 are formed on the silicon dioxide and silicon nitride layers 17 on the first surface 161. After patterning and electroless plating, to increase the system performance a gold layer 22 is formed on the nickel including conductive wires 113, antenna 151 and the pads of resistors 23. In one embodiment, the flexible substrate 16 may comprise plastic material such as polyethylene terephthalate (PET) or polyimide (PI).

The chip device 10 may be flip-chip bonded by thermal compression. Underfill material is applied and heated to dry for preventing dust and moisture from entering, and for preventing the chip device 10 from being detached by impact. By the way, the chip device 10, the antenna 151, and the conductive wires 113 can be coupled together more tightly.

Referring to FIGS. 7, 9, and 10, a resistor 156 can be formed on the flexible substrate 16. The resistor 156 comprises resistance material of patterned doped p-type polysilicon. The resistor 156 may be coupled to an oscillating module 153 formed in the chip device 10.

Figure 11:
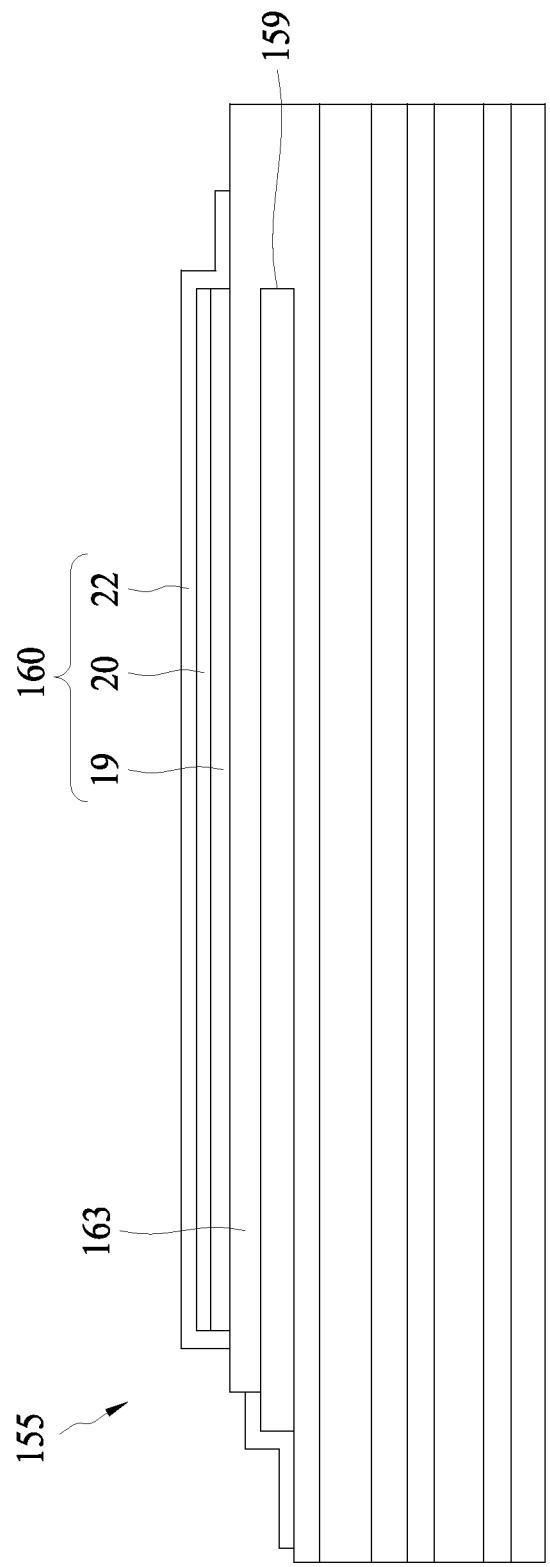
FIG. 11 is a view showing a thin film capacitor according to one embodiment of the present invention.

Referring to FIGS. 7 and 11, a capacitor 155 can be formed on the flexible substrate 16. The capacitor 155 may be coupled to a rectifying module 152 formed in the chip device 10 and may comprise a lower electrode layer 159, an upper electrode layer 160 and a dielectric layer 163 disposed between the lower and upper electrode layers 159 and 160. The upper electrode layer 160 may comprise a chromium layer 19, a nickel layer 20, and a gold layer 22. The lower electrode layer 159 may comprise doped p-type polysilicon. The dielectric layer 163 may comprise silicon nitride.

Referring to FIGS. 9 and 10, the flexible substrate 16 may include a plurality of openings, through which the probes 121 and 131 extend. The tip portions 122 and 132 extend out of the photoresist layer 18. Conductive wires 13 include a plurality of soldering pads 164. The top portions of the probes 122 and 132 opposite the tip portions 122 and 132 extend out from the soldering pads 164 and are covered by conductive paste material such as silver paste. The plurality of probes 121 and 131 can be respectively coupled to the pulse current generator 145 formed in the chip device 10 by conductive wires 110 and 113. When the probes 121 and 131 respectively contact the skin, loop circuits are formed.

Referring to FIGS. 9 and 10, two metal layers 114 and 115 can further be formed on the flexible substrate 16. The metal layer 115 can be formed on the first surface 161, electrically connecting to the plurality of probes 131 of the probe set 13. The metal layer 114 can be formed on the second surface 162 of the flexible substrate 16, electrically connecting to the probes 131. When the flexible substrate 16 is wrapped around a body portion, the metal layer 114 can contact the skin under which there is no acupuncture point (used as electrical ground), forming a ground loop, improving the performance of measuring acupuncture point impedance.

The bio-impedance measurement apparatus 1 can moreover comprise a battery 167 coupled to the chip device 10 for providing electricity required for operating the bio-impedance measurement apparatus 1 and to extend the communication and monitoring range. The battery 167 can be an AA battery, or a battery of small size such as a button-type battery suitable for use in a compact application.

Figure 2:
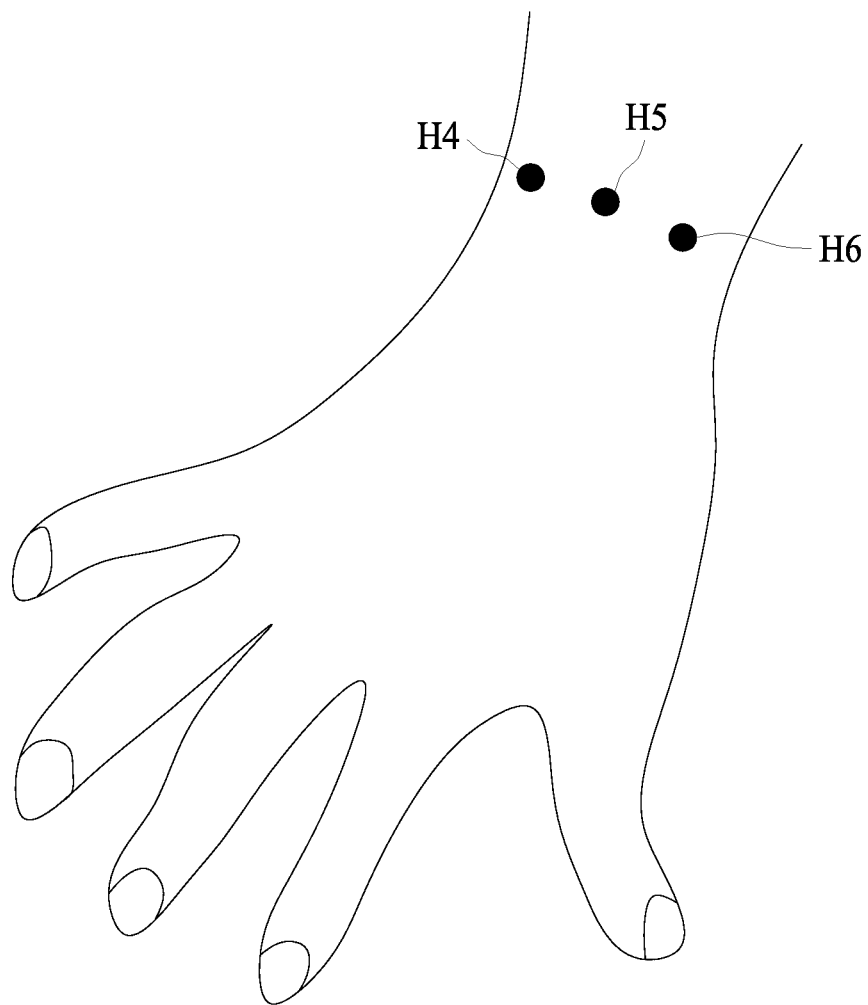
Figure 12:
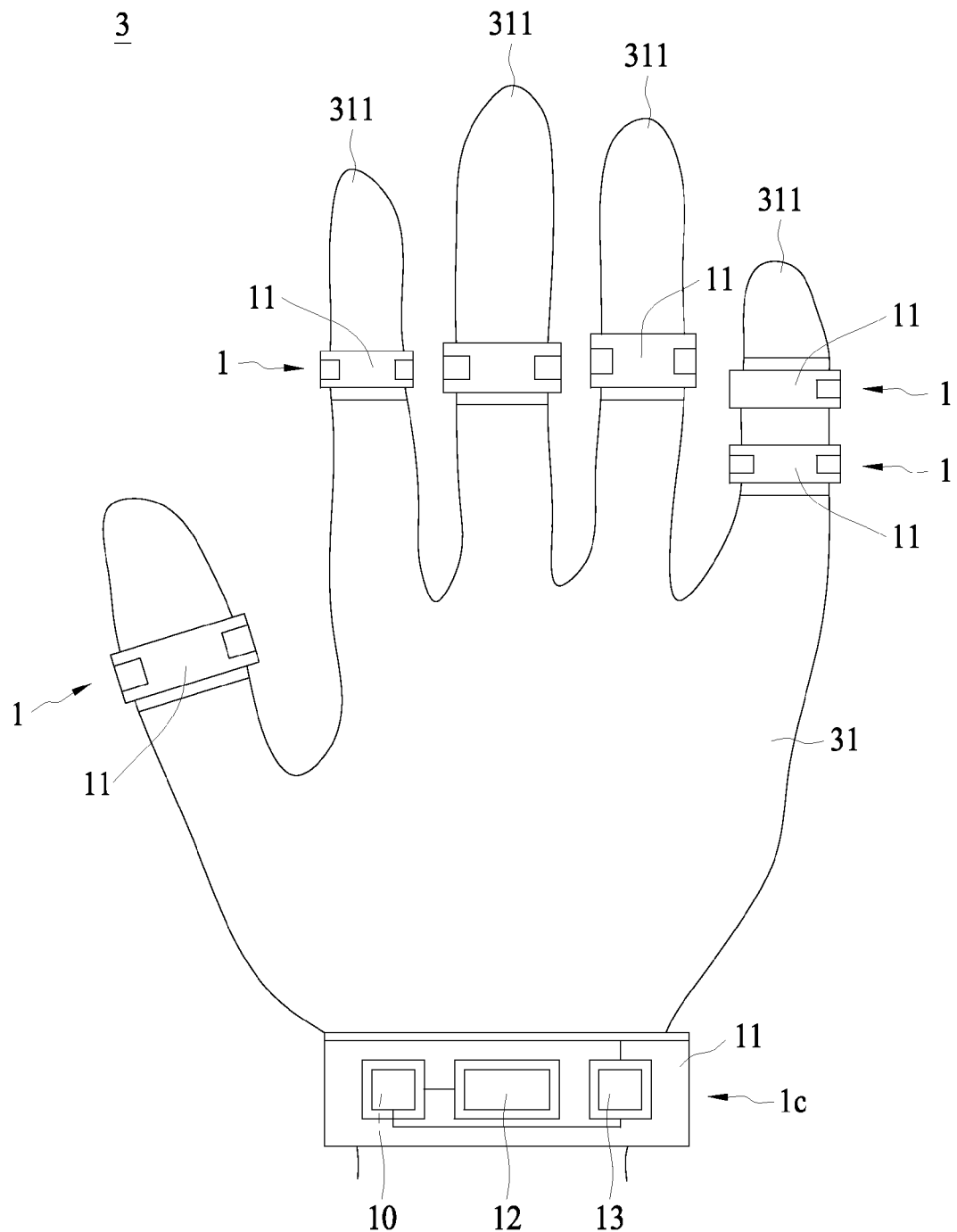
FIG. 12 is a view showing a bio-impedance measurement assembly according to one embodiment of the present invention.

FIG. 12 is a view showing a bio-impedance measurement assembly 3 according to one embodiment of the present invention. Referring to FIGS. 2 and 12, the bio-impedance measurement assembly 3 comprises a glove 31 and a plurality of bio-impedance measurement apparatuses 1 and 1c. The glove 31 may comprise a plurality of finger portions 311. The bio-impedance measurement apparatuses 1 are disposed on the finger portions 311 and corresponding to the acupuncture points on fingers. In addition, the bio-impedance measurement apparatuses 1c are disposed on the wrist portions and correspondingly with respect to the acupuncture points on wrist. The flexible band members 11 of the bio-impedance measurement apparatus 1 are fastened on the glove 31 and configured to be wrapped around fingers. The bio-impedance measurement apparatus 1c corresponding to the acupuncture points on the back of a wrist is disposed on the back side of the wrist section of the glove 31 and configured to be wrapped around a wrist. The bio-impedance measurement apparatus 1c can be arranged to measure the impedance of acupuncture points such as the acupuncture point H4, the acupuncture point H5, or the acupuncture point H6. The bio-impedance measurement assembly 3 can be worn on a hand and simultaneously measures the impedance of desired acupuncture points.

Figure 3:
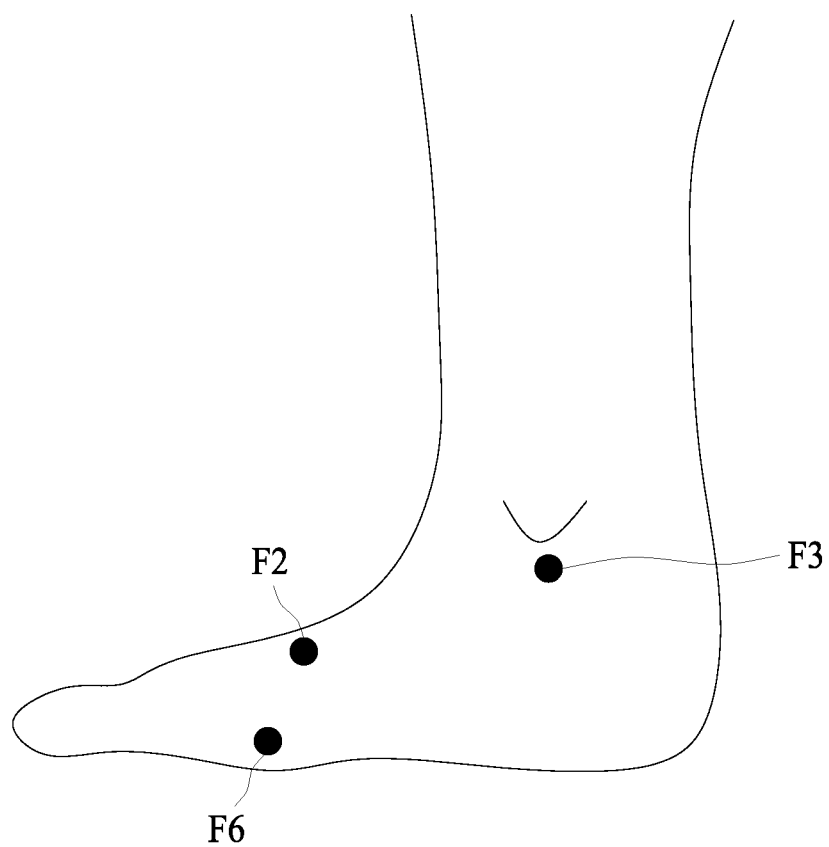
Figure 13:
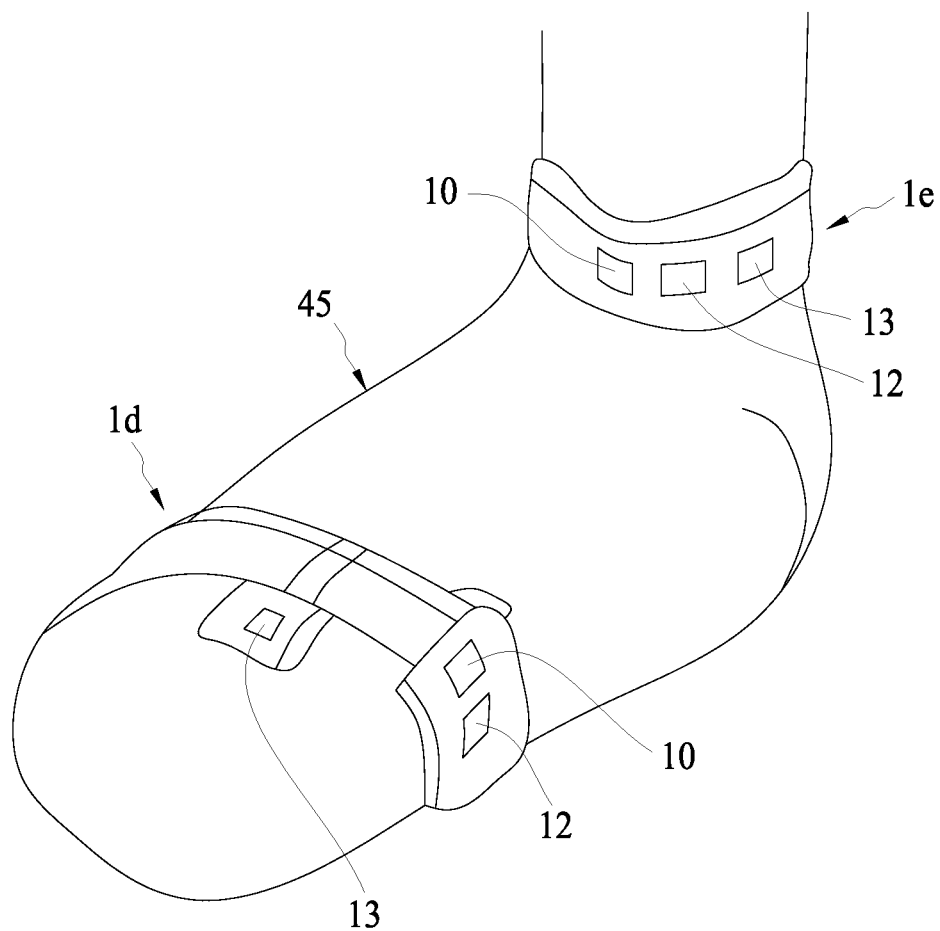
FIG. 13 is a view showing a bio-impedance measurement assembly according to another embodiment of the present invention.

FIG. 13 is a view showing a bio-impedance measurement assembly 4 according to another embodiment of the present invention. Referring to FIGS. 3 and 13, the bio-impedance measurement assembly 4 comprises a sock 45 and a plurality of bio-impedance measurement apparatuses 1d and 1e that can include flexible band members 11 for fastening on the sock 45. The flexible band member 11 is configured to be fastened around a foot portion. The bio-impedance measurement apparatus 1d is disposed with respect to the acupuncture points on the foot portion. The bio-impedance measurement apparatus 1*d* can be configured to be wrapped around a foot for measuring the impedance of the acupuncture point F2 or the acupuncture point F6. The bio-impedance measurement apparatus 1*e* is configured to be wrapped around a shank, close to the acupuncture point F3 of the ankle. The bio-impedance measurement assembly 4 can be worn directly on a foot and can measure the impedance of the desired acupuncture points on the foot.

Figure 14:
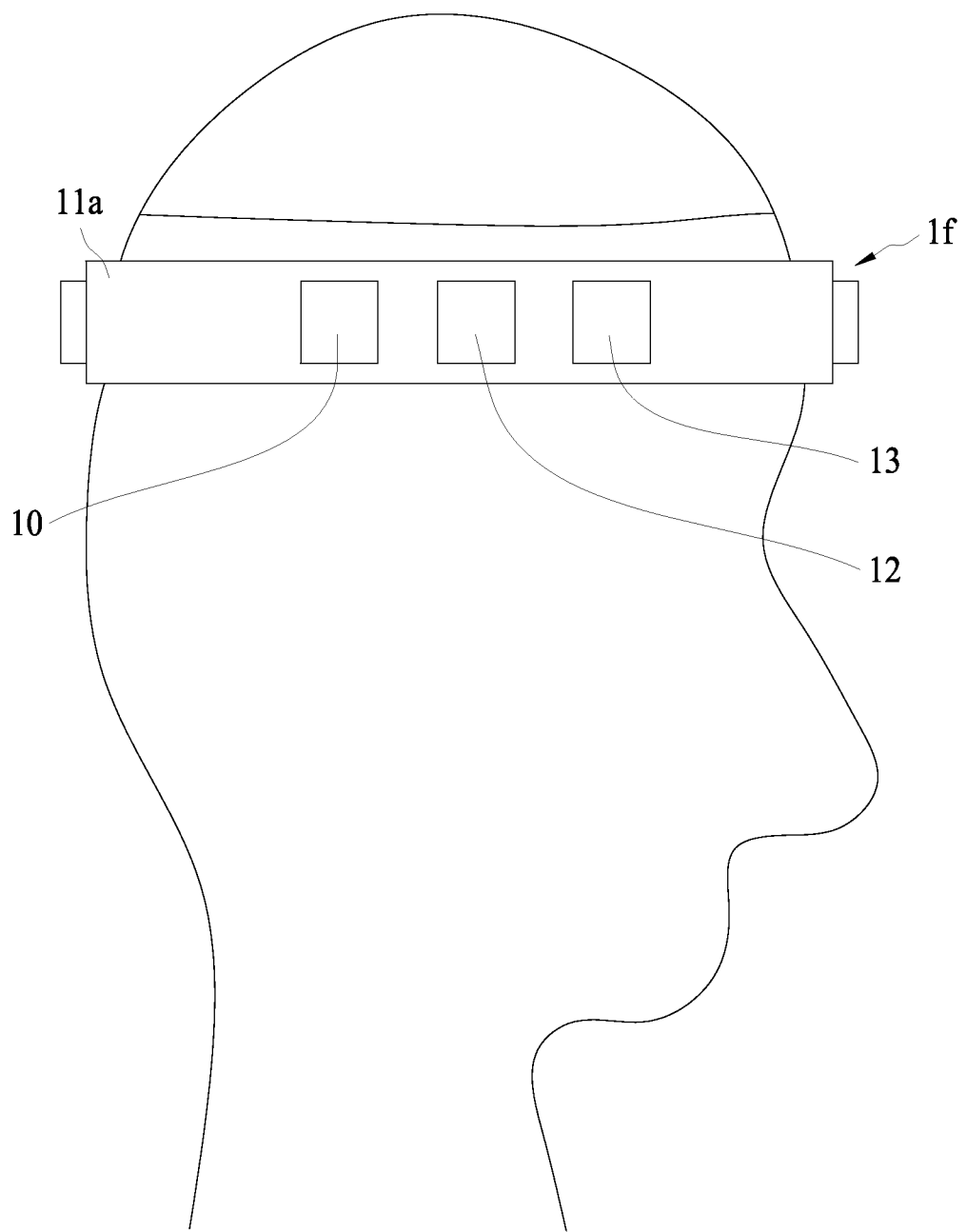
FIG. 14 is a view showing a bio-impedance measurement apparatus according to another embodiment of the present invention.

FIG. 14 is a view showing a bio-impedance measurement apparatus if according to another embodiment of the present invention. The bio-impedance measurement apparatus 1*f* comprises a flexible band member 11*a*, probe sets 12 and 13, and a chip device 10. The flexible band member 11*a* is configured to be wrapped around a head. The probe sets 12 and 13 are configured to measure desired acupuncture points. The chip device 10 is disposed on the flexible band member 11*a*, coupled to the probe sets 12 and 13 (the coupling circuit is not shown). The arrayed probes of the probe sets 12 and 13 have dimensions that allow the probes to extend through the flexible band member 11*a* and pierce into the dermis of the skin for better electrical contact.

Figure 16:
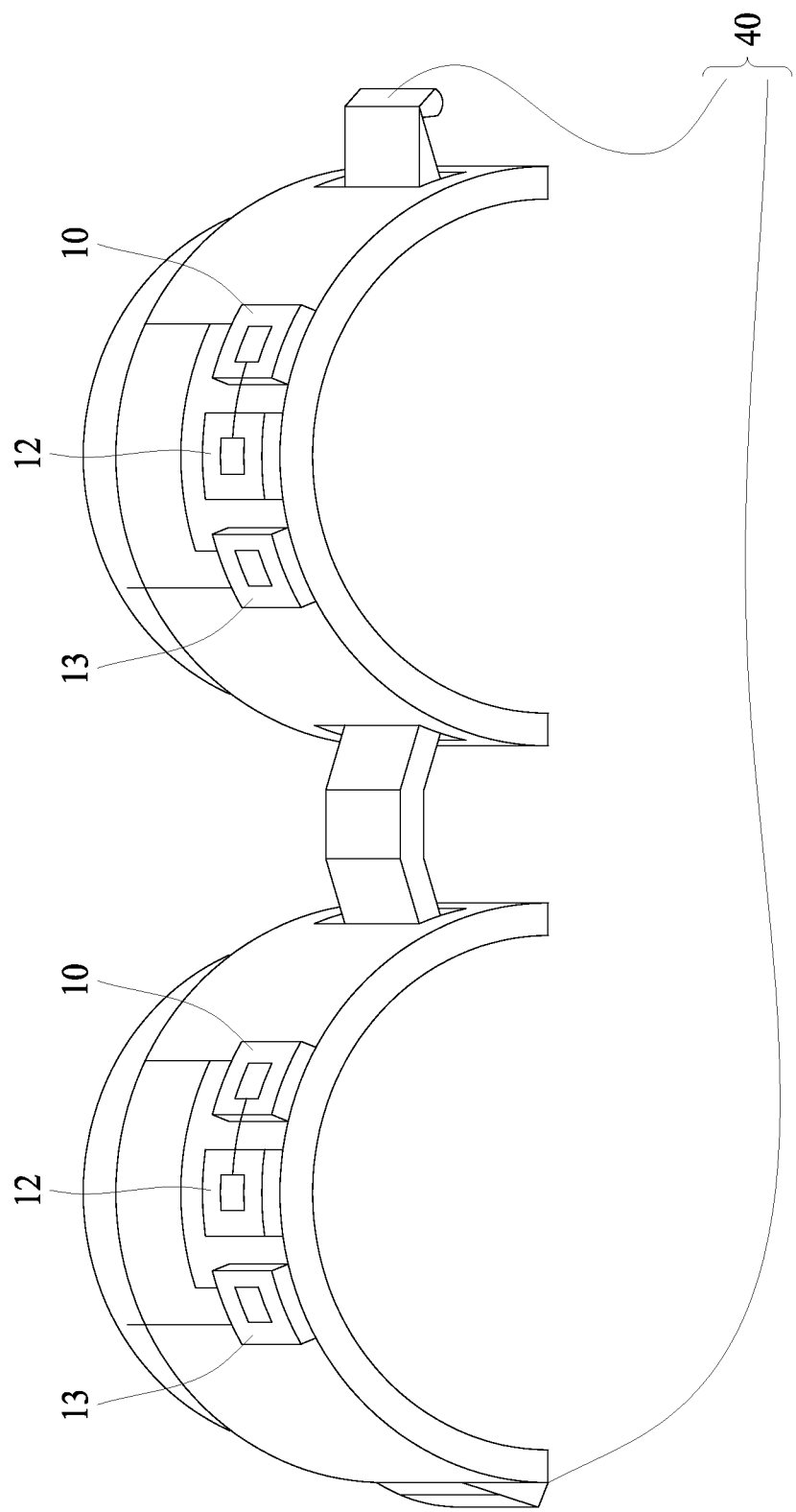
FIG. 16 demonstrates a buckle type fixture according to one embodiment of the present invention.
Figure 17:
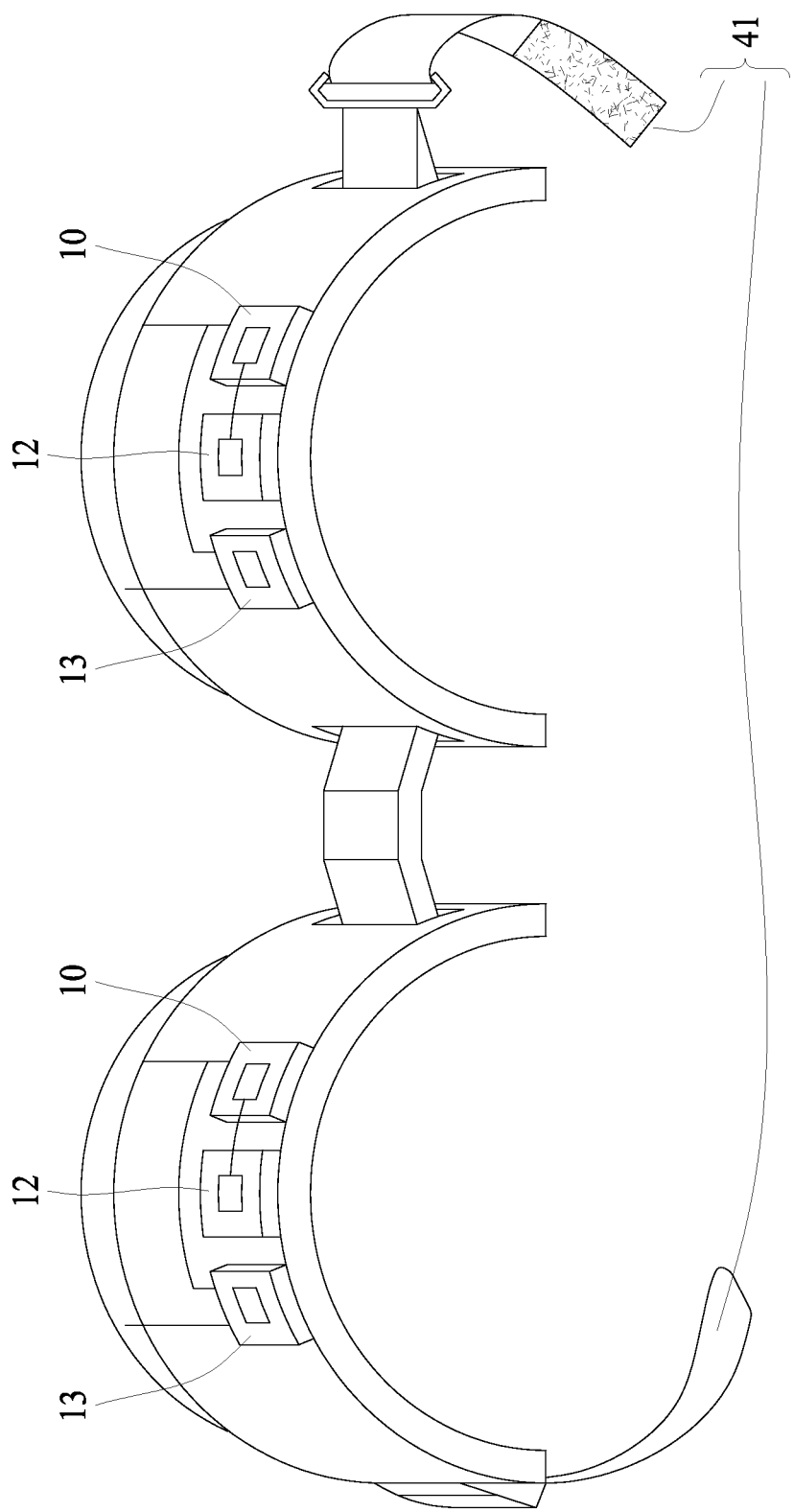
FIG. 17 demonstrates a fabric hook-and-loop fixture according to one embodiment of the present invention.
Figure 18:
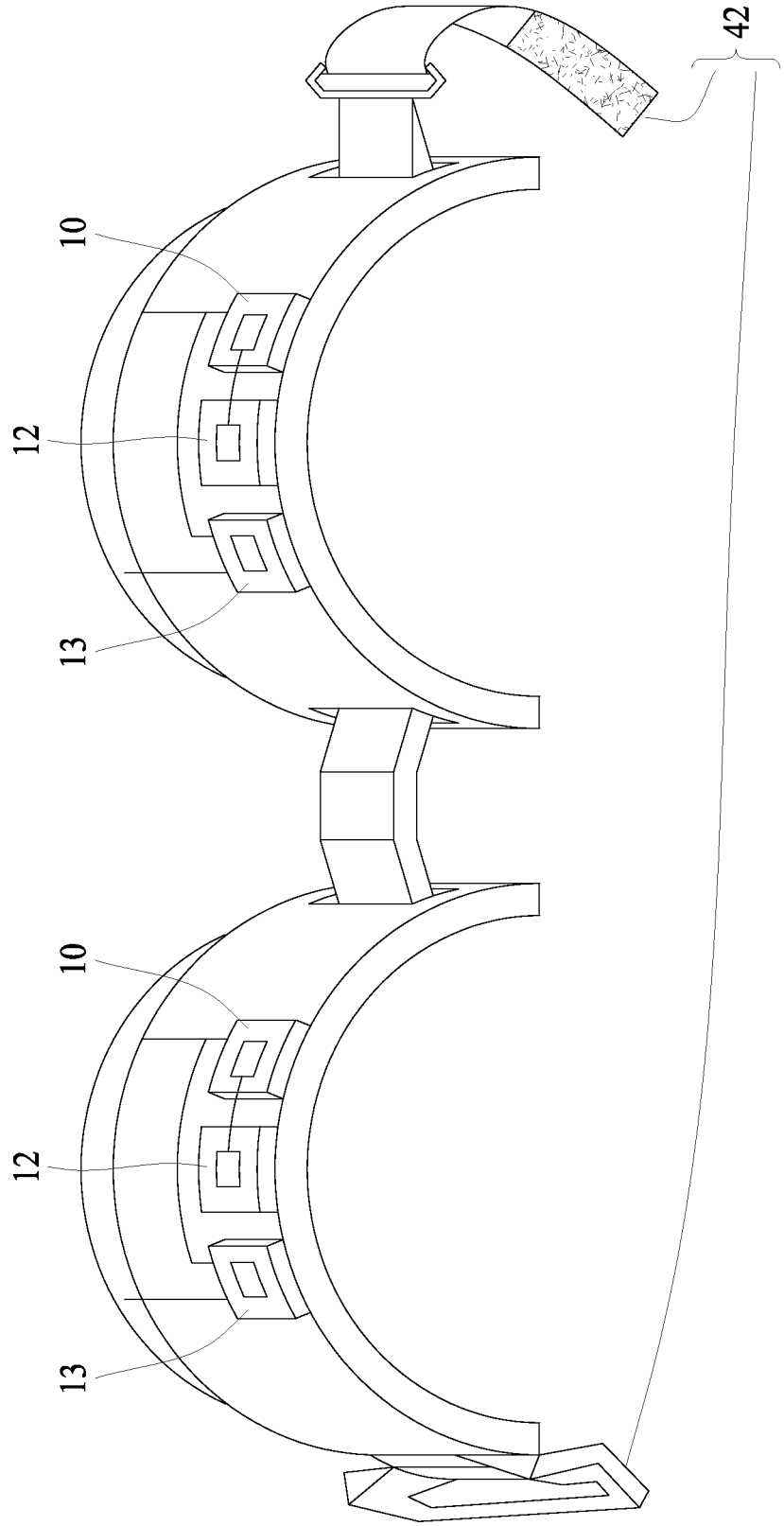
FIG. 18 demonstrates a fixture of fabric hook-and-loop with a buckle according to one embodiment of the present invention.
Figure 19:
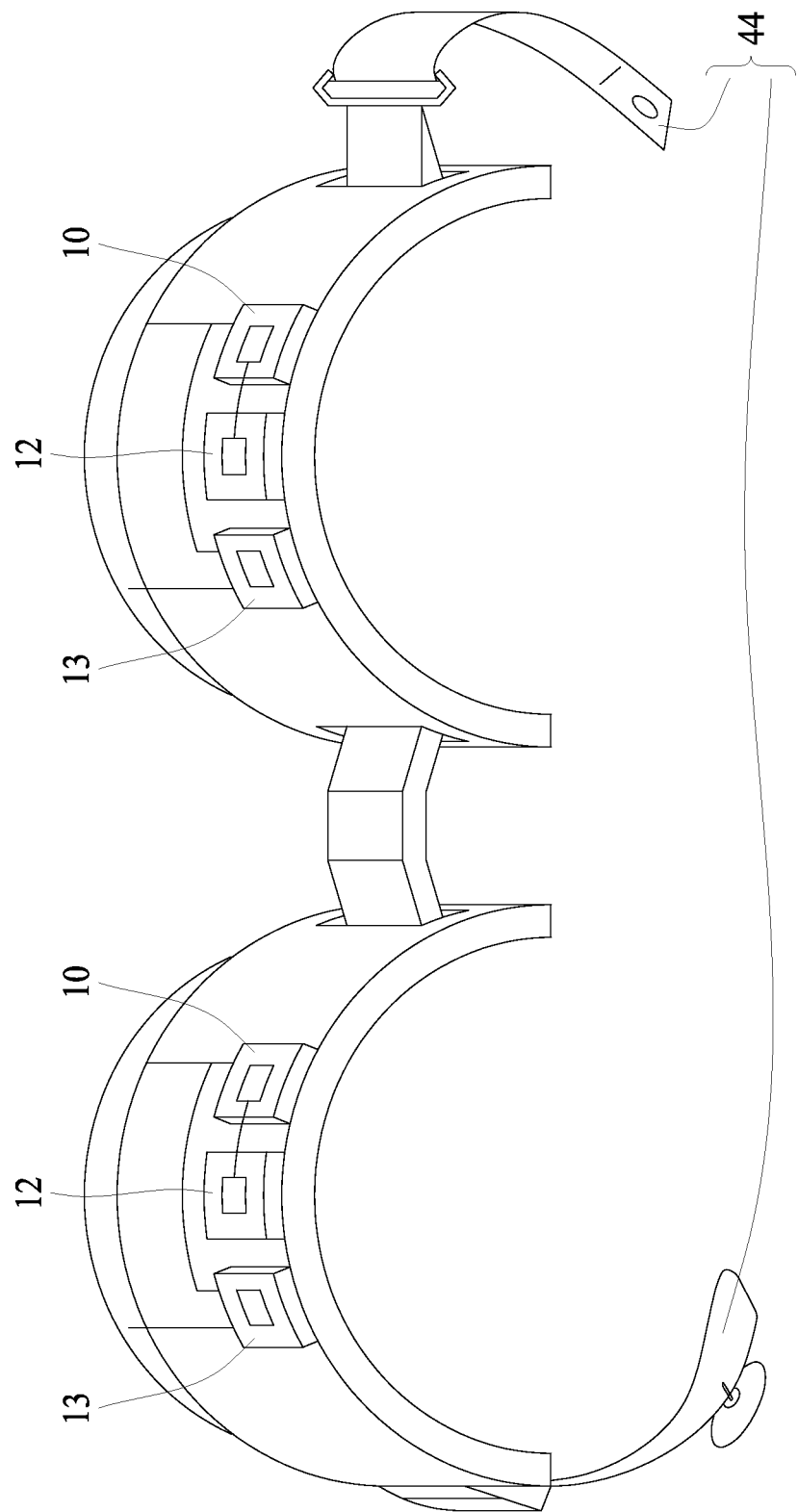
FIG. 19 demonstrates a button type fixture according to one embodiment of the present invention.

For easy installation of the apparatuses of the present invention to relevant portions of a human body, the present invention proposes a plurality of fixtures. The fixtures include a buckle type fixture 40 (FIG. 16), a fabric hook-and-loop fixture 41 (FIG. 17), a fixture of fabric hook-and-loop with a buckle 42 (FIG. 18), and a button type fixture 44 (FIG. 19). The fixtures can ensure that the arrayed probes of the probe sets 12 and 13 extend through the glove or sock and pierce into the dermis of the skin so as to establish good electrical contact.

In summary, the present invention discloses a bio-impedance measurement apparatus configured to measure the impedance of an acupuncture point comprising a wireless device that can transmit the codes and the impedance information of measured acupuncture points to a remote control station. The wireless device can be an RFID wireless device, a Zigbee wireless device, or a Bluetooth device. The bio-impedance measurement apparatus uses probes to measure the impedance of acupuncture points. The probes, preferably, can pierce into the dermis of the skin. The bio-impedance measurement apparatus comprises a flexible band member and a fixture. The flexible band member is configured to match a body portion so that the bio-impedance measurement apparatus can be wrapped around the body portion. The bio-impedance measurement apparatus can be associated with a glove or a sock so that acupuncture points on hands or feet can be simultaneously measured. The fixture can ensure that the arrayed probes of the probe sets extend through the glove or sock and pierce into the dermis of the skin so as to establish good electrical contact.

The above-described embodiments of the present invention are intended to be illustrative only. Numerous alternative embodiments may be devised by persons skilled in the art without departing from the scope of the following claims.

What is claimed is:

1. A wearable assembly for measuring bio-impedance coupled to a remote monitor station in a wireless manner, comprising:
   a glove comprising a plurality of finger portions; and
   a bio-impedance measurement apparatus disposed on one of the plurality of finger portions, the bio-impedance measurement apparatus comprising:
      a flexible band member configured to be fastened around a finger, comprising an inner surface adjacent to a skin region of the finger when the glove is worn;
      two probe sets attached to the flexible band member, each probe set comprising a probe, wherein the probe of one probe set includes a tip portion configured to protrude from the inner surface to pierce into the skin region so as to be located adjacent to an acupuncture point, and the probe of another probe is configured to contact the reference skin region as an electrical ground;
      a measurement device disposed on the flexible band member, electrically coupled to the two probe sets, configured to provide a signal to the acupuncture point and to measure impedance of the acupuncture point;
      a wireless device coupled to the measurement device, configured to transmit an acupuncture code corresponding to the acupuncture point and the impedance information of the acupuncture point to a remote monitor station;
      a fixture configured to ensure that the tip portion of the probe pierces through the glove and into the dermis of the skin to establish electrical connection, wherein the fixture is a buckle type fixture, a fabric hook-and-loop fixture, a fixture of fabric hook-and-loop with a buckle, or a button type fixture; and
      a battery device including a battery, configured to supply electricity for operating the bio-impedance measurement apparatus and to extend the communication and monitoring range;
      wherein the wireless device is coupled to an antenna and comprises:
         a rectifying module coupled to the antenna, configured to convert microwave energy into DC electricity;
         an oscillating module coupled to the antenna, configured to generate clock signals;
         a modulator coupled to the antenna, configured to modulate signals to be sent; and
         a thin film capacitor coupled to the rectifying module, wherein the rectifying module comprises a lower electrode layer comprising doped p-type polysilicon, an upper electrode layer, and a dielectric layer disposed between the lower and upper electrode layers;
         wherein the upper electrode layer comprises a chromium layer, a nickel layer and a gold layer, and the dielectric layer comprises silicon nitride.

2. The wearable assembly of claim 1, wherein the measurement device comprises:
   a pulse current generator coupled to the two probe sets for measuring the impedance of the acupuncture point;
   a voltage amplifier coupled to the pulse current generator to amplify voltage signals corresponding to the impedance of the acupuncture point;
   an analog/digital converter coupled to the voltage amplifier, configured to sample the voltage signals and output digital signals; and
   a processor coupled to the wireless device and to the analog/digital converter, configured to calculate the impedance of the acupuncture point using the digital signals and to send the acupuncture code and the impedance information of the acupuncture point to the wireless device.

3. The wearable assembly of claim 1, wherein the processor is configured to obtain the impedance of the acupuncture point by performing a Fourier transformation.

4. The wearable assembly of claim 1, wherein the remote monitor station is configured to obtain the impedance of the acupuncture point by performing a Fourier transformation.

5. A wearable assembly for measuring bio-impedance coupled to a remote monitor station in a wireless manner, comprising:
a sock; and
a bio-impedance measurement apparatus disposed on the sock, the bio-impedance measurement apparatus comprising:
a flexible band member configured to be fastened around a foot portion, comprising an inner surface adjacent to a skin region of the foot portion when the flexible band member fastened to the foot portion;
two probe sets attached to the flexible band member, each probe set comprising a probe, wherein the probe of one probe set includes a tip portion configured to protrude from the inner surface to pierce the skin so as to be located adjacent to an acupuncture point, and the probe of another probe set configured to contact the skin region as an electrical ground;
a measurement device disposed on the flexible band member, electrically coupled to the two probe sets, configured to provide a signal to the acupuncture point and to measure impedance of the acupuncture point;
a wireless device coupled to the measurement device, configured to transmit an acupuncture code corresponding to the acupuncture point and the impedance information of the acupuncture point to a remote monitor station;
a fixture configured to ensure that the tip portion of the probe pierces through the sock into the dermis of the skin to establish an electrical connection, wherein the fixture is a buckle type fixture, a fabric hook-and-loop fixture, a fixture of fabric hook-and-loop with a buckle, or a button type fixture; and
a battery device including a battery, configured to supply electricity for operating the bio-impedance measurement apparatus and to extend the communication and monitoring range;
wherein the wireless device is coupled to an antenna and comprises:
a rectifying module coupled to the antenna, configured to convert microwave energy into DC electricity;
an oscillating module coupled to the antenna, configured to generate clock signals;
a modulator coupled to the antenna, configured to modulate signals to be sent; and
a thin film capacitor coupled to the rectifying module, wherein the rectifying module comprises a lower electrode layer comprising doped p-type polysilicon, an upper electrode layer, and a dielectric layer disposed between the lower and upper electrode layers;
wherein the upper electrode layer comprises a chromium layer, a nickel layer and a gold layer, and the dielectric layer comprises silicon nitride.

6. The wearable assembly of claim 5, wherein the measurement device comprises:
a pulse current generator coupled to the two probe sets for measuring the impedance of the acupuncture point;
a voltage amplifier coupled to the pulse current generator, configured to amplify voltage signals corresponding to the impedance of the acupuncture point;
an analog/digital converter coupled to the voltage amplifier, configured to sample the voltage signals and output digital signals; and
a processor coupled to the wireless device and the analog/digital converter, configured to calculate the impedance of the acupuncture point using the digital signals and to send the acupuncture code and the impedance information of the acupuncture point to the wireless device.

7. The wearable assembly of claim 5, wherein the remote monitor station remotely controls the bio-impedance measurement to apparatus to provide the signal to the acupuncture point for measuring the impedance of the acupuncture point or to provide a treatment to the acupuncture point.

* * * * *